(12) United States Patent
Fry et al.

(10) Patent No.: US 7,252,992 B2
(45) Date of Patent: Aug. 7, 2007

(54) CELL LINE AND USES THEREOF

(75) Inventors: Dennis G. Fry, Gurnee, IL (US); Christine Ann Collins, Skokie, IL (US); Brian D. Dayton, Libertyville, IL (US)

(73) Assignee: Abbott Laboratories, Abbott Park, IL (US)

( * ) Notice: Subject to any disclaimer, the term of this patent is extended or adjusted under 35 U.S.C. 154(b) by 500 days.

(21) Appl. No.: 10/463,123

(22) Filed: Jun. 17, 2003

(65) Prior Publication Data

US 2004/0259194 A1 Dec. 23, 2004

(51) Int. Cl.
C12N 5/00 (2006.01)
C12N 5/10 (2006.01)
G01N 33/50 (2006.01)
G01N 33/566 (2006.01)

(52) U.S. Cl. ..................... 435/325; 435/7.21
(58) Field of Classification Search ............... None
See application file for complete search history.

(56) References Cited

OTHER PUBLICATIONS

Borowsky, B., et al., "Antidepressant, anxiolytic and anorectic effects of a melanin-concentrating hormone-1 receptor antagonist", *nature medicine*, 8(8):825-830 (2002).
Bradley, R. L., et al., "Melanin-concentrating hormone activates signaling pathways in 3T3-L1 adipocytes", *EJP—Endocrinology and Metab.*, 283:E584-E592 (2002).
Burgaud, J-L., et al., "Melanin-Concentrating Hormone Binding Sites in Human SVK14 Keratinocytes", *Biochem. And Biophys. Res. Comm.*, 241:622-629 (1997).
Griffond, B. and Baker, B.I., "Cell and Molecular Cell Biology of Melanin-Concentrating Hormone", *Intn'l Rev. of Cytology*, 213:233-277 (2002).
Hawes, B. E., et al., "The Melanin-Concentrating Hormone Receptor Couples to Multiple G Proteins to Activate Diverse Intracellular Signaling Pathways", *Endocrinology*, 141(12):4524-4532 (2000).

Kokkotou, E., et al., "Characterization of [Phe[13], Tyr[19]]-MCH analog binding activity to the MCH receptor", *Neuropeptides*, 34(3&4):240-247 (2000).
Saito, Y., et al., "Endogenous Melanin-Concentrating Hormone Receptor SLC-1 in Human Melanoma SK-MEL-37 Cells", *Biochem. & Biophys. Res. Comm.*, 280:44-50 (2001).
Tadayyon, M., et al., "Expression of Melanin-Concentrating Hormone Receptors in Insulin-Producing Cells: MCH Stimulates Insulin Release in RINm5F and CRI-G1 Cell-Lines", *Biochem. & Biophys. Res. Comm.*, 275:709-712 (2000).
Takahashi, K., et al., "Expression of Melanin-Concentrating Hormone Receptor Messenger Ribonucleic Acid in Tumor Tissues of Pheochromocytoma, Ganglioneuroblastoma, and Neuroblastoma", *Journ. Of Clin. Endoc. & Metab.*, 86(1):369-374 (2001).
Takekawa, S., et al., "T-226296: a novel, orally active and selective melanin-concentrating hormone receptor antagonist", *Eur. Journ. Of Pharm.*, 438:129-135 (2002).
Rostomily, R.C., et al., "Expression of Neurogenic Basic Helix-Loop-Helix Genes in Primitive Neuroectodermal Tumors[1]", *Cancer Research*, 57(16):3526-3531 (1997).
Schlumberger, S.E., et al., "Endogenous receptor for melanin-concentrating hormone in human neuroblastoma Kelly cells", *Biochem & Biophy Res Comm.*, 298:54-59 (2002).
Shimomura, Y., et al., "Isolation and Identification of Melanin-Concentrating Hormone as the Endogenous Ligand of the SLC-1 Receptor", *Biochem & Biophys Res Comm.*, 261:622-626 (1999).
Tumilowicz, J.J., "Definition of a Continuous Human Cell Line Derived from Neuroblastoma", *Cancer Research*, 30(8):2110-2118 (1970).
"Melanin-concentrating hormone receptor 1", *Databsae UniProt*, XP002316310 (1992).

*Primary Examiner*—David S Romeo
*Assistant Examiner*—Daniel C Gamett
(74) *Attorney, Agent, or Firm*—Cheryl L. Becker

(57) ABSTRACT

The subject invention relates to a novel cell line, referred to as T4240213.4.2, and to uses of this cell line. For example, the cell line may be used in the production of recombinant melanin concentrating hormone (MCH) receptor protein and in the identification of antagonists, inverse agonists and agonists to the receptor.

11 Claims, 3 Drawing Sheets

FIGURE 1 a. AMINO ACID SEQUENCE OF MCHR₁ DEDUCED FROM T4240213.4.2 GENOMIC DNA

MDLEASLLPTGPNASNTSDGPDNLTSAGSPPRTGSISYINIIMPSVFGTICLLGII
GNSTVIFAVVKKSKLHWCNNVPDIFIINLSVVDLLFLLGMPFMIHQLMGNGV
WHFGETMCTLITAMDANSQFTSTYILTAMAIDRYLATVHPISSTKFRKPSVAT
LVICLLWALSFISITPVWLYARLIPFPGGAVGCGIRLPNPDTDLYWFTLYQFFL
AFALPFVVITAAYVRILQRMTSSVAPASQRSIRLRTKRVTRTAIAICLVFFVCW
APYYVLQLTQLSISRPTLTFVYLYNAAISLGYANSCLNPFVYIVLCETFRKRLV
LSVKPAAQGQLRAVSNAQTADEERTESKGT* b. EXPRESSION OF MCHR₁ MRNA IN PARENT IMR32 CELLS AND T4240213.4.2 CELLS

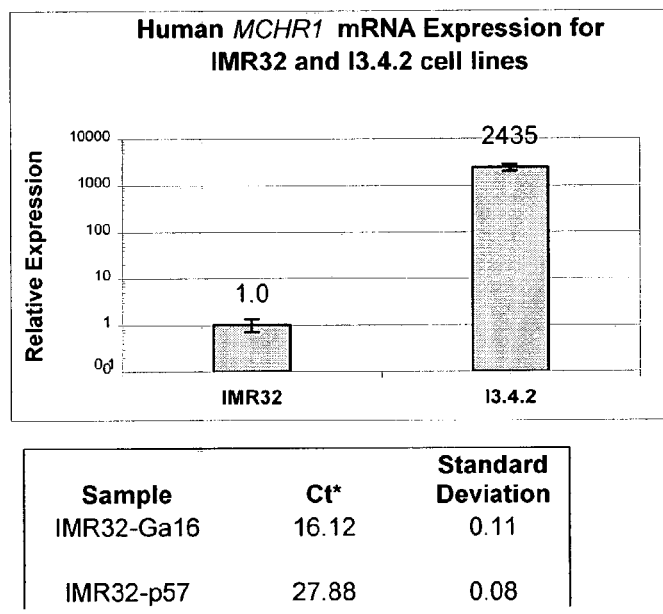

FIGURE 2
$Ca^{++}$-FLUX RESPONSE OF I3.4.2 CELLS TO MCH
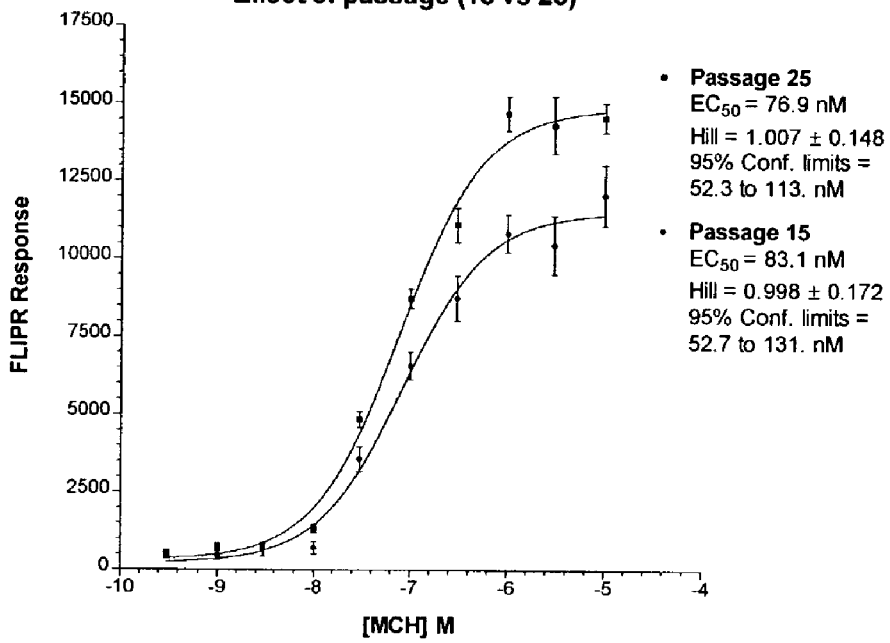
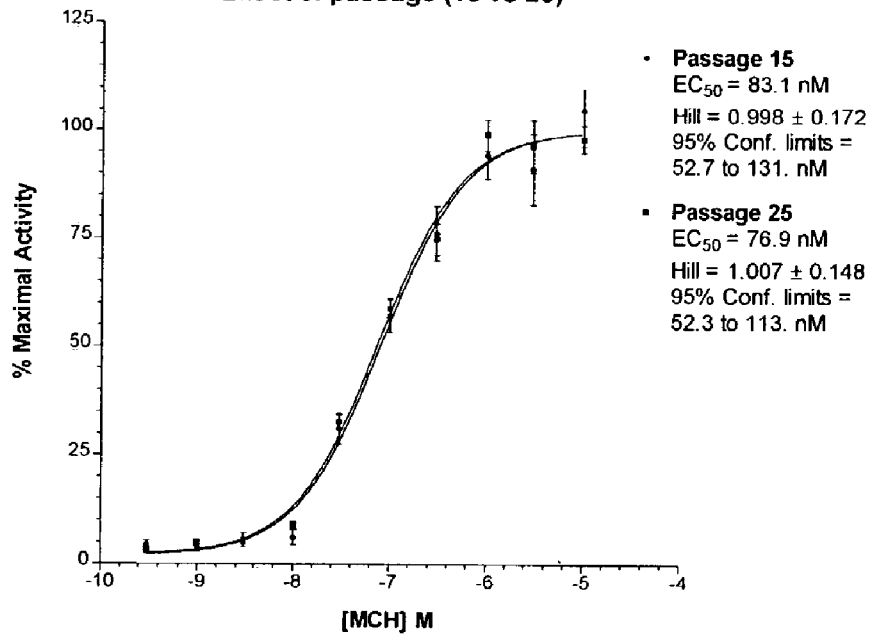

INHIBITION OF MCHR$_1$-MEDIATED SIGNALING IN I3.4.2 CELLS BY KNOWN MCHR$_1$-ANTAGONISTS

SEQUENCE LISTING

<160> NUMBER OF SEQ ID NOS: 17

<210> SEQ ID NO 1
<211> LENGTH: 353

-continued

```
<212> TYPE: PRT
<213> ORGANISM: Homo sapiens

<400> SEQUENCE: 1

Met Asp Leu Glu Ala Ser Leu Leu Pro Thr Gly Pro Asn Ala Ser Asn
 1               5                  10                  15

Thr Ser Asp Gly Pro Asp Asn Leu Thr Ser Ala Gly Ser Pro Pro Arg
            20                  25                  30

Thr Gly Ser Ile Ser Tyr Ile Asn Ile Ile Met Pro Ser Val Phe Gly
            35                  40                  45

Thr Ile Cys Leu Leu Gly Ile Ile Gly Asn Ser Thr Val Ile Phe Ala
 50                  55                  60

Val Val Lys Lys Ser Lys Leu His Trp Cys Asn Asn Val Pro Asp Ile
65                  70                  75                  80

Phe Ile Ile Asn Leu Ser Val Val Asp Leu Leu Phe Leu Leu Gly Met
                85                  90                  95

Pro Phe Met Ile His Gln Leu Met Gly Asn Gly Val Trp His Phe Gly
            100                 105                 110

Glu Thr Met Cys Thr Leu Ile Thr Ala Met Asp Ala Asn Ser Gln Phe
            115                 120                 125

Thr Ser Thr Tyr Ile Leu Thr Ala Met Ala Ile Asp Arg Tyr Leu Ala
130                 135                 140

Thr Val His Pro Ile Ser Ser Thr Lys Phe Arg Lys Pro Ser Val Ala
145                 150                 155                 160

Thr Leu Val Ile Cys Leu Leu Trp Ala Leu Ser Phe Ile Ser Ile Thr
                165                 170                 175

Pro Val Trp Leu Tyr Ala Arg Leu Ile Pro Phe Pro Gly Gly Ala Val
            180                 185                 190

Gly Cys Gly Ile Arg Leu Pro Asn Pro Asp Thr Asp Leu Tyr Trp Phe
            195                 200                 205

Thr Leu Tyr Gln Phe Phe Leu Ala Phe Ala Leu Pro Phe Val Val Ile
210                 215                 220

Thr Ala Ala Tyr Val Arg Ile Leu Gln Arg Met Thr Ser Ser Val Ala
225                 230                 235                 240

Pro Ala Ser Gln Arg Ser Ile Arg Leu Arg Thr Lys Arg Val Thr Arg
                245                 250                 255

Thr Ala Ile Ala Ile Cys Leu Val Phe Phe Val Cys Trp Ala Pro Tyr
            260                 265                 270

Tyr Val Leu Gln Leu Thr Gln Leu Ser Ile Ser Arg Pro Thr Leu Thr
            275                 280                 285

Phe Val Tyr Leu Tyr Asn Ala Ala Ile Ser Leu Gly Tyr Ala Asn Ser
290                 295                 300

Cys Leu Asn Pro Phe Val Tyr Ile Val Leu Cys Glu Thr Phe Arg Lys
305                 310                 315                 320

Arg Leu Val Leu Ser Val Lys Pro Ala Ala Gln Gly Gln Leu Arg Ala
                325                 330                 335

Val Ser Asn Ala Gln Thr Ala Asp Glu Glu Arg Thr Glu Ser Lys Gly
            340                 345                 350

Thr

<210> SEQ ID NO 2
<211> LENGTH: 20
<212> TYPE: DNA
<213> ORGANISM: Artificial Sequence
<220> FEATURE:
```

```
<223> OTHER INFORMATION: PCR primers

<400> SEQUENCE: 2
ctcagctcgg ttgtgggagc                                               20

<210> SEQ ID NO 3
<211> LENGTH: 20
<212> TYPE: DNA
<213> ORGANISM: Artificial Sequence
<220> FEATURE:
<223> OTHER INFORMATION: PCR primer

<400> SEQUENCE: 3
aggcgaccgg cactggctgg                                               20

<210> SEQ ID NO 4
<211> LENGTH: 27
<212> TYPE: DNA
<213> ORGANISM: Artificial Sequence
<220> FEATURE:
<223> OTHER INFORMATION: PCR primer

<400> SEQUENCE: 4
atggacctgg aagcctcgct gctgccc                                       27

<210> SEQ ID NO 5
<211> LENGTH: 20
<212> TYPE: DNA
<213> ORGANISM: Artificial Sequence
<220> FEATURE:
<223> OTHER INFORMATION: PCR primer

<400> SEQUENCE: 5
ggtggcgtgt tgtggtgccc                                               20

<210> SEQ ID NO 6
<211> LENGTH: 17
<212> TYPE: DNA
<213> ORGANISM: Artificial Sequence
<220> FEATURE:
<223> OTHER INFORMATION: PCR primer

<400> SEQUENCE: 6
gacttggagg tgtgcag                                                  17

<210> SEQ ID NO 7
<211> LENGTH: 27
<212> TYPE: DNA
<213> ORGANISM: Artificial Sequence
<220> FEATURE:
<223> OTHER INFORMATION: PCR primer

<400> SEQUENCE: 7
tcaggtgcct ttgctttctg tcctctc                                       27

<210> SEQ ID NO 8
<211> LENGTH: 20
<212> TYPE: DNA
<213> ORGANISM: Artificial Sequence
<220> FEATURE:
<223> OTHER INFORMATION: PCR primer

<400> SEQUENCE: 8
tttctgtcct ctcctcgtca                                               20
```

```
<210> SEQ ID NO 9
<211> LENGTH: 20
<212> TYPE: DNA
<213> ORGANISM: Artificial Sequence
<220> FEATURE:
<223> OTHER INFORMATION: PCR primer

<400> SEQUENCE: 9
ctgtagcaca tagtagggtg                                           20

<210> SEQ ID NO 10
<211> LENGTH: 20
<212> TYPE: DNA
<213> ORGANISM: Artificial Sequence
<220> FEATURE:
<223> OTHER INFORMATION: PCR primer

<400> SEQUENCE: 10
tatgccgcag cccactgcac                                           20

<210> SEQ ID NO 11
<211> LENGTH: 20
<212> TYPE: DNA
<213> ORGANISM: Artificial Sequence
<220> FEATURE:
<223> OTHER INFORMATION: PCR primer

<400> SEQUENCE: 11
aagatgaccg tggagttccc                                           20

<210> SEQ ID NO 12
<211> LENGTH: 20
<212> TYPE: DNA
<213> ORGANISM: Artificial Sequence
<220> FEATURE:
<223> OTHER INFORMATION: PCR primer

<400> SEQUENCE: 12
gctgccgcag cctgcgtggg                                           20

<210> SEQ ID NO 13
<211> LENGTH: 20
<212> TYPE: DNA
<213> ORGANISM: Artificial Sequence
<220> FEATURE:
<223> OTHER INFORMATION: PCR primer

<400> SEQUENCE: 13
accagctcat gggcaatggg                                           20

<210> SEQ ID NO 14
<211> LENGTH: 20
<212> TYPE: DNA
<213> ORGANISM: Artificial Sequence
<220> FEATURE:
<223> OTHER INFORMATION: PCR primer

<400> SEQUENCE: 14
gcatgacgtc ctcagtggcc                                           20

<210> SEQ ID NO 15
<211> LENGTH: 18
<212> TYPE: DNA
<213> ORGANISM: Artificial Sequence
<220> FEATURE:
<223> OTHER INFORMATION: PCR primer
```

-continued

```
<400> SEQUENCE: 15
gcagtgggct gcggcata                                              18

<210> SEQ ID NO 16
<211> LENGTH: 24
<212> TYPE: DNA
<213> ORGANISM: Artificial Sequence
<220> FEATURE:
<223> OTHER INFORMATION: PCR primer

<400> SEQUENCE: 16
aaactggtac agggtgaacc agta                                       24

<210> SEQ ID NO 17
<211> LENGTH: 25
<212> TYPE: DNA
<213> ORGANISM: Artificial Sequence
<220> FEATURE:
<223> OTHER INFORMATION: PCR primer

<400> SEQUENCE: 17
cctgcccaac ccagacactg acctc                                      25
```

CELL LINE AND USES THEREOF

BACKGROUND OF THE INVENTION

1. Technical Field

The subject invention relates to a novel cell line, referred to as T4240213.4.2, and to uses of this cell line. For example, the cell line may be used in the production of non-recombinant, melanin-concentrating hormone (MCH) receptor protein and in the identification of antagonists, inverse agonists and agonists to the receptor.

2. Background Information

The recombinant MCH receptor has been expressed in a variety of cell lines and these cell lines have been utilized to elucidate potential intracellular signaling pathways from the receptor (Griffond and Baker, *Int. Rev. Cytol.* 213:233-277 (2002) and Hawes et al., *Endocrinology* 141:4524-4532 (2000)). Further, a number of cell lines have been reported to express $MCHR_1$ mRNA and/or to bind $^{125}$I-MCH or exhibit MCH-mediated receptor activation (Bradley et al., *Am. J. Physiol. Endocrinol. Metab.* 283:E584-E592 (2002); Burgaud et al., *Biochem. Biophys. Res. Commun.* 241:622-629 (1997); Saito et al., *Biochem. Biophys. Res. Commun.* 289:44-50 (2001); Tadayyon et al., *Biochem. Biophys. Res. Commun.* 275:709-712 (2000) and Takahashi et al., *J. Clin. Endocrinol. Metabol.* 86:369-374 (2001)). However, some of the reports of MCH-binding to various cell lines may not be correct due to the high level of non-specific binding that is observed with some of the $^{125}$I-labelled peptides used in published studies (Kokkotou et al., *Neuropeptides* 34:240-247 (2000)).

Use of the recombinant receptor to discover small-molecule antagonists of MCH receptor activation has also been reported (Takekawa et al., *Eur. J. Pharmacol.* 438:129-135 (2002) and Borowsky et al., *Nature Medicine* 8:825-830 (2002)).

In view of the above, there is a significant need to discover methods of production of the receptor. Once the receptor is produced, for example, it may be utilized to find antagonists, agonists and inverse agonists related thereto. It may also be utilized to elucidate the physiological pathways in which the receptor is involved.

All U.S. patents and publications referred to herein are hereby incorporated in their entirety by reference.

SUMMARY OF THE INVENTION

The present invention includes an isolated cell line referred to as T4240213.4.2 ("I.3.4.2") and having A.T.C.C. deposit designation PTA-5201 as well as the isolated protein produced by cells of the cell line. In particular, the protein is the melanin-concentrating hormone (MCH) receptor. The present invention also encompasses compositions comprising cells of the cell line or membranes of the cells.

Additionally, the present invention also encompasses a cell line that maintains responsiveness to MCH for greater than ten culture passages. MCH may be native human MCH peptide or MCH of other species, e.g. salmon MCH, or altered forms of said MCH peptide, e.g., by amino acid deletions, substitutions, or modifications, such that the resulting peptide maintains its ability to bind to $MCHR_1$ with a $K_d$ of <100 nM. The cell line also exhibits an $EC_{50}$ of approximately 90 nM for MCH-mediated calcium $^{++}$-mobilization. Also, the invention includes a composition comprising cells of this cell line.

Further, the present invention encompasses a method of producing MCH receptor comprising the steps of culturing cells of the above cell line, or a cell line derived therefrom, for a time and under conditions sufficient for production of the MCH receptor.

Additionally, the present invention includes a method of identifying an antagonist or inverse agonist to the MCH receptor (MCHR) comprising the steps of: a) contacting cells of cell line T4240213.4.2 with a test compound for a time and under conditions sufficient for the test compound to bind to MCHR produced by the cells; b) adding MCH to said contacted cells of step (a); and c) measuring intracellular calcium influx in the cells of step (a) as compared to cells of this cell line which have not been exposed to the test compound, a decrease in intracellular calcium influx in the contacted cells of step (a) as compared to cells of the cell line which have not been exposed to the test compound indicating the test compound is an antagonist or inverse agonist to the MCH receptor. Also, the present invention includes any MCHR antagonist or inverse agonist identified in accordance with this method.

Moreover, the present invention encompasses a method of identifying an agonist to the MCH receptor comprising the steps of: a) contacting cells of cell line T4240213.4.2 with a test compound for a time and under conditions sufficient for the test compound to bind to MCHR produced by cells of the cell line; and b) measuring intracellular calcium influx in the cells of step (a) as compared to cells of the cell line which have not been exposed to the test compound, an increase in the intracellular calcium influx in the cells of step (a) as compared to cells of the cell line which have not been exposed to the test compound indicating the test compound is an agonist to the MCH receptor. The invention also includes any agonist identified by this method.

Additionally, the present invention includes a method of inhibiting activation of intracellular signaling by MCH comprising contacting cells of cell line T4240213.4.2 with an antagonist to MCHR for a time and under conditions sufficient for the antagonist to bind to MCHR produced by cells of the cell line, binding inhibiting activation of intracellular signaling by MCH subsequently added to the contacted cells of the cell line.

Also, the present invention includes a method of determining the affinity of binding of MCH to MCHR comprising the steps of: a) contacting cells of cell line T4240213.4.2, or membranes thereof, with a conjugate of MCH, wherein the conjugate comprises MCH attached to a signal-generating compound capable of generating a detectable signal for a time and under conditions sufficient for MCHR produced by cells of the cell line to bind to the MCH of the conjugate; b) adding unlabelled MCH to the bound MCHR, for a time and under conditions sufficient for the unlabelled MCH to displace the conjugate and, in particular, the MCH of the conjugate; and c) detecting intensity of a signal generated by the signal-generating compound, wherein intensity of the signal is proportional to displacement of the conjugated MCH, by the unlabelled MCH, and indicates the binding affinity of the MCH of the conjugate to the MCHR.

Further, the present invention includes a method of identifying a composition that inhibits binding of MCH to MCHR comprising the steps of: a) contacting cells of cell line T4240213.4.2, or membranes thereof, with a test compound suspected of inhibiting binding of MCH to MCHR for a time and under conditions sufficient for the test compound to bind to MCHR produced by cells of the cell line; b) adding a conjugate to the contacted cells of the cell line of step (a), wherein the conjugate comprises MCH attached to a signal-generating compound capable of generating a measurable signal; and c) measuring inhibition of binding of MCH to MCHR by the test compound by quantifying the generated measurable signal and comparing the generated measurable signal to a control signal produced in the absence of the test compound, the control signal indicating zero percent inhibition of binding of MCH to MCHR, a smaller signal obtained with use of the test compound as compared to the control signal, indicating the test compound partially or completely inhibits binding of MCH to MCHR.

The present invention also encompasses a method of distinguishing between an antagonist and an inverse agonist of MCHR comprising the steps of a) contacting cells of cell line T4240213.4.2 or membranes thereof with a test compound suspected of inhibiting activation of MCHR for a time and under conditions sufficient for the test compound to bind to MCHR produced by cells of the cell line; b) adding a conjugate to the contacted cells of step (a), wherein the conjugate comprises MCH attached to a signal-generating compound capable of generating a measurable signal; and c) measuring inhibition of a basal level of activity of MCHR by the test compound by quantifying the generated measurable signal and comparing the generated measurable signal to a control signal produced in the absence of the test compound. The control signal indicates basal activity of MCHR; thus, a smaller signal obtained with use of the test compound as compared to the control signal indicates the compound is an inverse agonist of MCHR, and an equal signal obtained with use of the test compound as compared to the control signal indicates the compound is an antagonist of MCHR.

Additionally, the present invention includes a method for producing a cell line that expresses MCHR. This method comprises the steps of: a) contacting IMR32 cells with DNA encoding $G\alpha_{16}$ and an antibiotic resistance marker; b) adding antibiotic for the antibiotic resistance marker to the contacted cells; c) isolating antibiotic resistant cells of step (b) and propagating the isolated cells; d) adding to the propagated cells the antibiotic at a higher concentration than used in step (b); and e) isolating resulting cells of step (d) and propagating the isolated cells in order to produce a cell line that produces MCHR. The increasing concentrations of the antibiotic serve to stabilize expression of the genes encoding the MCHR, $G\alpha_{16}$ and antibiotic resistance marker.

BRIEF DESCRIPTION OF THE DRAWINGS

FIG. 1a shows the amino acid sequence of $MCHR_1$ from the I3.4.2 cells (SEQ ID NO:1), deduced from the genomic $MCHR_1$ DNA sequence, and FIG. 1b illustrates a qPCR analysis of MCHR expression in parental and I3.4.2 cells.

FIG. 2 illustrates a dose response curve of the I3.4.2 cell line to MCH.

DETAILED DESCRIPTION OF THE INVENTION

Figure 3:
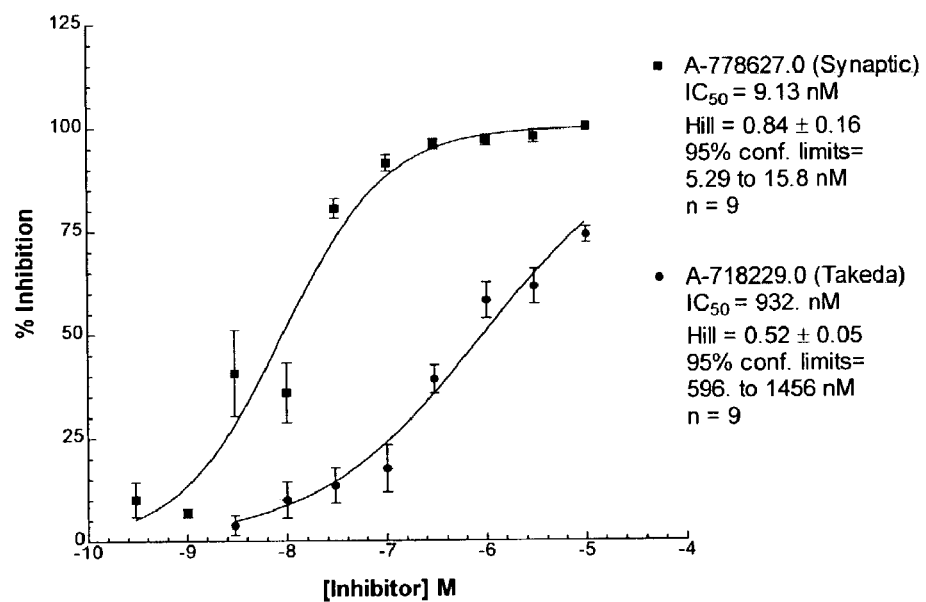
FIG. 3 illustrates inhibition of MCH-induced $Ca^{++}$-flux by two $MCHR_1$ antagonists.

The subject invention relates to a genetically engineered cell line referred to as T4240213.4.2 (or "I3.4.2"), the cells of which produce the MCH receptor or protein. The cell line was derived from the IMR32 cell line (having ATTCC deposit designation number CCL-127, available from the American Type Culture Collection, 10801 University Boulevard, Manassas, Va. 20110-2209) via transfection of a plasmid encoding the $G\alpha_{16}$ protein. IMR32 is a human neuroblastoma cell line that expresses melanin-concentrating hormone receptor (MCHR) mRNA (see Takahashi et al., supra (2001)); however, there was an inability to detect intracellular signaling in response to MCH in the IMR32 cell line.

The novel cell line maintains responsiveness to MCH for greater than ten culture passages and exhibits an EC50 of approximately 90 nM for MCH-mediated $Ca^{++}$-mobilization (as measured using a fluorometric imaging plate reader (Molecular Devices, Sunnyvale, Calif.)). Sequence analysis (FIG. 1a) indicates that the $MCHR_1$ sequence encoded in the I3.4.2 cell line is the same as that described in the literature (Griffond and Baker, supra (2002)). Unexpectedly, cells of the I3.4.2 cell line express a much higher level of $MCHR_1$ mRNA than cells of the parent IMR32 cell-line, as shown by qPCR analysis (FIG. 1b).

In particular, the cell line may be useful in the production of the MCH receptor; for the discovery and development of MCH receptor agonists, inverse agonists and antagonists and also for studying the effects of MCH, MCHR agonists, MCHR inverse agonists and MCHR antagonists on a neurally-derived cellular model in vitro. Such a cell line may be a more relevant cell type for the study of a neuropeptide receptor antagonist or agonist than the more commonly used HEK or CHO fibroblast cell lines expressing recombinant receptors. Further, the discovery of MCH antagonists, for example, may be expected to lead to drugs for weight loss by decreasing food intake through action on MCH receptors located in the feeding centers of the brain and/or promoting increased energy expenditure.

It should also be noted that many intracellular signaling pathways are affected by the presence of MCH. Thus, a compound that binds to the MCH receptor and prevents activation thereof will alter the natural course or outcome of such pathways. Consequently, the present cell line may be used in the identification of antagonists or inverse agonists which affect these pathways. For example, the cell line may be used in the identification of antagonists or inverse agonists to the receptor which then prevent MAPK activation and phosphotidylinositol hydrolysis and allow cAMP accumulation (i.e., by-products or end-products in the pathways). Alternatively, if one wishes to positively affect these pathways, one may use the cell line in order to identify agonists which enhance the function of the MCH receptor.

In connection with the hormone itself, MCH is a 19 amino acid cyclic neuropeptide that has been shown to regulate food intake and energy homeostasis in rodents. When injected intracerebrally into the hypothalamus of rodents, MCH stimulates food intake. Expression of MCH mRNA is elevated in genetically obese ob/ob mice and transgenic mice that overexpress MCH are hyperphagic and obese. Conversely, transgenic mice that do not express MCH ($MCH^{-/-}$) are hypophagic and lean. Mice that do not express the MCH receptor ($MCHR^{-/-}$), although not hypophagic, remain lean when fed a high-fat diet, (Chen et al, *Endocriol.* 143:2469-2477 (2002); Marsh et al., *Proc. Natl. Acad. Sci. USA* 98:3240-3245 (2002)).

The present invention may be illustrated by the use of the following non-limiting examples:

EXAMPLE I

Creation of the Cell Line and Determination of Cell-Signaling

IMR32 cells (ATCC#CCL-127) were cultured in minimum essential medium (MEM)/10% fetal bovine serum/50

μg/ml/gentamycin (growth medium). Twenty-four hr prior to transfection, the cells were plated into 24-well tissue culture plates at 200,000 cells/well. For transfection, DNA of a plasmid encoding Gα16 and a Zeocin resistance marker was mixed with Lipofectoamine2000 in serum-free MEM according to manufacturer's recommendations (Invitrogen, Grand Island, N.Y.). This solution was applied to IMR32 cells in culture media. Six hours later, this transfection medium was removed and replaced with fresh culture medium. Twenty-four hours later, the cells were trypsinized, resuspended and replated into 6-well culture plates at approximately one-fourth the original cell density.

The following day, Zeocin (Invitrogen, Carlsbad, Calif.) was added to a final concentration of 20 μg/ml. Cells were maintained in this medium with periodic replacement until discrete colonies were observed. Individual colonies were isolated and propagated until sufficiently large cell populations were obtained such that the cell samples could be cryopreserved. After cryopreservation, the cells were assessed for MCH-mediated signaling. Such signaling was determined using an assay similar to that described in Example III in connection with $Ca^{++}$-mobilization, except that antagonist compounds were not included in the assay and varying concentrations of MCH (1 nM to 10 μM) (Bachem, King of Prussia, Pa.) were applied to the cells to determine an $EC_{50}$ for receptor activation.

The cell line obtained initially (i.e., I3.4) did not exhibit a stable response to MCH. Over the course of 3-4 culture passages, the cells' response to MCH fell to undetectable levels in the $Ca^{++}$-mobilization assay.

Such phenotypic instability is not unusual for transfected cell lines due to the high rate of genetic modification occurring in such cell populations. Reselection and subcloning of the initial cell line sometimes allow the isolation of a more stable variant from within the original cell population. The use of a higher concentration of selective agent increases the selective pressure for a high level of expression of the drug-resistance transgene. Since the unselected transgene, in this case, $Gα_{16}$, is closely linked genetically to the drug-resistance transgene, this reselection process tends to select for clonal variants that exhibit a high level of expression of both the marker gene and the unselected transgene. Therefore, in order to recover a MCH-responsive cell line, cryopreserved cells were thawed and subsequently reselected for Zeocin resistance at 200 μg/ml in an effort to obtain a cell line with more stable expression of the desired phenotype. Individual cell colonies were isolated, propagated and assayed as described above.

The resulting cell line, T4240213.4.2, maintained responsiveness to MCH, as measured using the $Ca^{++}$-mobilization assay, for greater than ten culture passages. Typical $EC_{50}$ curves for the cells are shown in FIG. 2. The $EC_{50}$ was found to be 80 nM (SEM=12, n=8), a value that is comparable to literature reports of $EC_{50}$s for cell lines expressing recombinant $MCHR_1$ (Chambers et al., *Nature* 400:261-265 (1999); Saito et al., *Nature* 400:265-269 (1999); Lembo, *Nature Cell Biol.* 1:267-271 (1999); Hawes et al., *Endocriol.* 141:4524-4532 (2000)).

The I3.4.2 cell line of the present invention was deposited with the American Type Culture Collection, 10801 University Boulevard, Manassas, Va. 20110-2209 on May 15, 2003 under the terms of the Budapest Treaty and has received deposit designation PTA-5201.

EXAMPLE II $MCHR_1$ Sequence and mRNA Expression in I3.4.2 Cells

The $MCHR_1$ sequence was determined for I3.4.2 cells. Briefly, confluent cells were washed with D-PBS to remove growth medium, lysed with 5 mL Trizol reagent (Invitrogen, Carlsbad, Calif.) and RNA prepared following the manufacturer's protocol. The resulting RNA was treated with RQ1 DNase (Promega, Madison, Wis.) to reduce the level of contaminating DNA. RNA was reverse transcribed with Superscript II (Invitrogen, Carlsbad, Calif.) following manufacturer's recommended protocol, in duplicate, to make cDNA as a substrate for PCR. cDNA was amplified using Platinum PFX polymerase (Invitrogen, Carlsbad, Calif.) with the PCR primers listed below:

```
5' outer
CTC AGC TCG GTT GTG GGA GC          (SEQ ID NO:2)

5' inner
AGG CGA CCG GCA CTG GCT GG          (SEQ ID NO:3)

5' cds
ATG GAC CTG GAA GCC TCG CTG CTG CCC (SEQ ID NO:4)

3' outer
GGT GGC GTG TTG TGG TGC CC          (SEQ ID NO:5)

3' inner
GAC TTG GAG GTG TGC AG              (SEQ ID NO:6)

3' cds
TCA GGT GCC TTT GCT TTC TGT CCT CTC (SEQ ID NO:7)
```

PCR cycling conditions were: 1 cycle of 2 min at 94° C.; 30 cycles of 30 sec at 94° C./30 sec at 50° C./2 min at 68° C.; and 1 cycle of 10 min at 68° C. Following initial amplification using the outer primers, a 1 μL sample from this initial PCR amplification was re-amplified (30 cycles) using the nested (inner) primer set listed above. Products from the nested PCR reaction were electrophoresed on an agarose gel, and the highest molecular weight band obtained was gel purified and sequenced. Although the products of the amplification reaction were larger than expected based on the reported size of the $MCHR_1$ transcript, DNA was sequenced from eight independently generated PCR products using the primers listed below and Perkin-Elmer Big Dye cycle sequencing technology (Applied Biosystems, Foster City, Calif.) following manufacturer's recommended protocol.

Sequencing Primers:

```
mchr1 seq 3.1
5'- TTT CTG TCC TCT CCT CGT CA      (SEQ ID NO:8)

mchr1 seq 3.2
5'- CTG TAG CAC ATA GTA GGG TG      (SEQ ID NO:9)

mchr1 seq 3.3
5'- TAT GCC GCA GCC CAC TGC AC      (SEQ ID NO:10)

mchr1 seq 3.4
5'- AAG ATG ACC GTG GAG TTC CC      (SEQ ID NO:11)

mchr1 seq 5.1
5'- GCT GCC GCA GCC TGC GTG GG      (SEQ ID NO:12)

mchr1 seq 5.2
5'- ACC AGC TCA TGG GCA ATG GG      (SEQ ID NO:13)
```

-continued

```
mchr1 seq 5.3
5'- GCA TGA CGT CCT CAG TGG CC    (SEQ ID NO:14)
```

DNA sequencing results indicated that the sequenced bands were obtained from genomic DNA, probably the result of incomplete RQ1 digestion. Since the genomic sequence contains only one short intron, amplification of trace genomic DNA was not an unlikely outcome of the procedure used. The sequence obtained is identical to GENBANK sequence NM_005297. The predicted amino acid sequence is shown in FIG. 1a (SEQ ID NO:1).

The relative expression of human $MCHR_1$ mRNA in I3.4.2 and the parental IMR32 cell lines was quantitated using TaqMan® Real Time qPCR methodology using the ABI Prism 7700 (Applied Biosystems). Gene specific (GSP) TaqMan® primers and probes for the human $MCHR_1$ gene were designed using the Primer Express program (Applied Biosystems) and synthesized using standard phosphoramidite chemistry. All GSP TaqMan® probes were 5' labeled with the reporter fluorescein (FAM) and 3' labeled with the quencher tetramethylrhodamine (TAMARA). Total cell RNA was prepared with Trizol Reagent as described by the manufacturer and treated with Dnase I (Invitrogen, Carlsbad, Calif.) to remove any contaminating genomic DNA. The Qiagen QuantiTect Probe RT-PCR kit® (Qiagen, Valencia, Calif.) was used per manufacturer's instructions to detect the $MCHR_1$ transcripts. The 69 bp $MCHR_1$ amplicon was amplified using the following primers:

```
forward primer
5'- GCAGTGGGCTGCGGCATA -3'        (SEQ ID NO:15)

reverse primer
5'- AAACTGGTACAGGGTGAACCAGTA -3'  (SEQ ID NO:16)

TaqMan ® probe
5'-[FAM] CCTGCCCAACCCAGACACTGACCTC  (SEQ ID NO:17)
                                     [TAMRA].
```

Amplification was carried out in triplicate in a 25 µL reaction volume containing 100 ng of total RNA in an optical PCR plate for thermal cycling. QRTPCR reaction conditions were as follows: 1 cycle of 30 min at 50° C./15 min at 95° C., followed by 40 cycles of 15 sec at 94° C./1 min at 60° C. Data were collected during the PCR extension phase and analyzed with the ABI-7700 SDS 1.6.3 software package. The data were normalized to the internal control, 28S rRNA amplification. Using the 28S rRNA and $MCHR_1$ data for each sample, the ΔΔCt method (PE-ABI Prism 7700 Users Bulletin Number 2) was employed to compare the relative expression values of the I3.4.2 cells with the IMR32 parental cell line. The results (FIG. 1b) indicate that the I3.4.2 cell line expresses the $MCHR_1$ transcript at greater than 1000-fold the level detected in the parental IMR32 cell line.

EXAMPLE III $Ca^{++}$-Mobilization Assay Using I3.4.2 Cells

Activation of the melanin concentrating hormone receptor (MCHR) by melanin-concentrating hormone (MCH) induces the release of $Ca^{++}$ from intracellular stores. This intracellular calcium release is measured using a fluorometeric imaging plate reader (FLIPR™, Molecular Devices Corp., Sunnyvale, Calif.) in conjunction with the $Ca^{++}$-sensitive dye reagent (Calcium Assay Reagent, Molecular Devices Corp., Sunnyvale, Calif.). Release of $Ca^{++}$ from intracellular stores causes an increase in fluorescence of the dye that is proportional to $Ca^{++}$ concentration. Thus, this method may be utillized to identify agonist-s, antagonists, and inverse agonists of $MCHR_1$.

Routinely, the percent inhibition of $Ca^{++}$-mobilization by a test compound will be determined at final test-compound concentrations of 0.1 µM and 2 µM, rather than by determining $IC_{50}$ values. This procedure will increase the rate and number of compounds that can be screened for activity. $IC_{50}$ values can be obtained for selected, high priority test compounds using essentially the same assay procedure by testing multiple concentrations of a test-compound. To confirm the utility of the cell line described herein for the assay outlined above, the $IC_{50}$'s were determined for two $MCHR_1$ antagonists, T-226296 (developed by Takeda Chemical Industries, Tsukuba, Japan) and SNAP-7941 (developed by Synaptic Pharmaceutical Corp., Paramus, N.J.), recently described in the literature (Takekawa et al., Europ. J. Pharmacol. 438: 129-135 (2002); Borowsky et al., Nature Medicine 8:793-800 (2002)). In those publications, these compounds were shown to inhibit binding of $^{125}$I-labeled MCH to $MCHR_1$ and activation of intracellular signaling by MCH. Our results (see FIG. 3) demonstrate that MCH-stimulated intracellular $Ca^{++}$-flux in the T4240213.4.2 cell line is inhibited, as expected, by the $MCHR_1$ antagonists T-226296 and SNAP-7941.

In particular, the assay is carried out as follows: The cells are cultured in MEM/10% fetal bovine serum/50 µg/mL gentamicin/200 µg/ml Zeocin. The cells are plated at 100,000 cells/well in poly-D-lysine coated, 96 FLIPR™ assay plates (BD Biosciences, Bedford, Mass. After two days, cells are loaded with the Calcium Assay Reagent for one hour at 37° C. Test compounds are prepared at 60 µM in 6% dimethyl sulfoxide. The cell plate is placed in the FLIPR™, and 50 µl/well of test compound is delivered. The calcium signal is followed for 3 minutes to assay for potential agonist activity by the test compounds. Then, 50 µl/well of 6 µM human MCH (in Dulbecco's phosphate-buffered saline (PBS) containing 0.1% bovine serum albumin (BSA)) is added, and the ligand-induced calcium signal is followed for an additional 3 minutes. Antagonist activity, as determined by the test compound's ability to inhibit MCH-induced $Ca^{++}$ flux, is calculated as percent inhibition as described by the following formula:

$$\% \text{ inhibition} = [1 - ((fTC - fB)/(fMCH - fB))] \times 100$$

fTC=MCH-induced fluorescence in the presence of test compound;

fMCH=MCH-induced fluorescence in the absence of test compound; and fB=baseline fluorescence.

MCH (1 µM) usually elicits a response of 5,000-6,000 relative fluorescence units (RFU) with a baseline of approximately 700 RFU. Calcium Assay Reagent fluorescence is measured at 488 nm, with an exposure of 0.40 sec. and F-stop=2.0 and the laser set at 0.20-0.40 W constant light output. It should be noted that both antagonists and inverse agonists would be expected to produce similar results in this assay. Both types of agent have been found to be useful therapeutically for inhibition of signaling by various GPCR.

EXAMPLE IV

Ligand-Binding Assay

Various assays to measure binding of a ligand to its receptor and its inhibition are widely utilized and well known to those skilled in the art. Binding of MCH to $MCHR_1$ can be measured using such assays. The assay also may be used to identify inhibitors of MCH binding. Such inhibitors may be peptides or small-molecule compositions. For example, $^{125}$I-MCH (or MCH labeled with a fluorescent molecule, biotin, other radiolabel, etc.) may be used as a tracer, and $MCHR_1$ may be presented on the surface of an intact cell. Cells are removed from the culture substrate using Non-enzymatic cell dissociation buffer (Invitrogen, Grand Island, N.Y.) and counted using a hemocytometer. The cell density is adjusted to $2.2\times10^6$ cells/mL using binding buffer (25 mM HEPES, pH 7.4, 1 mM $CaCl_2$, 5 mM $MgCl_2$, 0.5% BSA) and 89 µL/well of cell suspension is added to a 96-well polypropylene v-bottom microtiter plate. Test compounds (1 µl) or unlabeled MCH, diluted in 100% DMSO, are added to the wells for a final concentration of 0 to 10 µM followed by 10 µl of $^{125}$I-MCH (PerkinElmer, Boston, Mass.). The final concentration of $^{125}$I-MCH in each well is 50 pM. The plate is then placed on a titer plate shaker for 1 hour at room temperature. The samples are then transferred to a 0.1% PEI (polyethylenimine, Sigma) treated glass fiber filter plate using a Packard Filtermate Harvestor (PerkinElmer, Boston, Mass.). The filter plate is washed three times using 200 µl wash buffer (Binding buffer without BSA and with 0.5M NaCl). Microscint 20 (PerkinElmer, Boston, Mass.) is added to all wells and the plate is sealed with adhesive film (Topseal A, PerkinElmer, Boston, Mass.). CPM is measured from the plate using a microplate scintillation counter (Topcount, PerkinElmer, Boston, Mass.). The ability of a test compound to compete with the labeled-MCH for binding to $MCHR_1$ is calculated as follows:

% inhibition=$[1-((CPM_T-CPM_0)/(CPM_B-CPM_0))]\times 100$ $CPM_T$=CPM in the presence of test compound
$CPM_B$=CPM in the absence of competitor
$CPM_0$=non-specific binding, i.e., CPM in the presence excess unlabeled-MCH compound, typically >1000-fold the concentration of labeled-MCH.

Modifications of this assay, well known to those skilled in the art, may be used to determine dissociation constants for the native ligand or inhibitor compounds.

It should also be noted that, in the above assay, the labeled MCH could be replaced by a suitably labeled, small-molecule or peptidomimetic compound or sequence-modified MCH-related peptide. Such assays are well known and widely used for assessment of ligand-binding to GPCRs. For example, measurement of ligand binding to the $\alpha_1$-adrenergic receptor may be accomplished using labeled prazosin (Greengrass and Bremner, Eur. J. Pharmacol. 55:1323-326 (1979)), ligand-binding to the endothelin A receptor may be accomplished using labeled BQ-123 (Ihara et al, Eur. J. Pharmacol., 274:1-6 (1995)), and ligand-binding to the neurotensin receptor may be accomplished using labeled SR-48692 (Betancur et al, Eur. J. Pharmacol. 343:67-77 (1998)).

EXAMPLE V

Inverse Agonist Assay

Inverse agonists (e.g., reverse agonists and negative agonists) are compounds that reduce the activity level of a receptor below the basal activity state (i.e., the activity level in the absence agonist) for that receptor (Strange, Trends in Pharmacol. Sci. 23:89-95 (2002)). As mentioned in Example III above, inverse agonists and antagonists will exhibit similar activities in the $Ca^{++}$-mobilization assay. Discriminating between these classes of compounds can be challenging, particularly when the basal activity of the target receptor is low. However, the differentiation of inverse agonists from antagonists may be useful for understanding in vivo properties of compounds identified as inhibitors of $MCHR_1$ signaling. Inverse agonists exhibit preferential binding to the inactive state of the receptor and, thus, suppress agonist-independent binding of GTP to the receptor. Binding of GTP to the receptor-G-protein complex may be measured using a non-hydrolysable GTP analog such as [$^{35}$S]GTP-γS or Eu-labeled GTP. Briefly, such an assay may be accomplished as follows. $MCHR_1$ containing membranes are isolated from I3.4.2 cells using a standard membrane preparation method (Bouaboula et al, J. Biol. Chem., 272:22330-22339 (1997)). I3.4.2 cell membranes (1-20 µg) are incubated with 10 µM GDP, labeled GTP (0.01-0.1 µM), and test compound or MCH in a buffer (50 mM Tris-HCl, pH7.4, 3 mM $MgCl_2$, 0.2 mM ethylene glycol-bis(β-aminoethyl ether)-N,N,N',N'-tetraacetic acid (EGTA), 100 mM NaCl, and 0.1% bovine serum albumin) for an appropriate interval. The reaction mixture is then filtered through glass-fiber membrane, washed to remove non-bound labeled GTP and the binding of labeled GTP is detected using an appropriate instrument, i.e., scintillation counter for [$^{35}$S]GTP-γS or time-resolved fluorometer for Eu-GTP. Resulting data is generally reported relative to basal activity:

% activation=$[((S_{tc}-NSB)\times 100))\div(S_b-NSB)]-100$ $S_{tc}$=signal in presence of test compound
$S_b$=basal signal in the absence of MCH
NSB=non-specific binding; signal in the presence of excess unlabeled-GTP-γS Using this method, an inverse agonist produces a signal less than the basal signal resulting in 'negative activation', i.e., % activation less than zero. A classic antagonist would be expected to have little or no effect on the basal activity measured in this assay. Other assays using various methods (de Ligt et al, Br. J. Pharmacol., 130:1-12(2000)) described in the literature also may be Used with the I3.4.2 cells (or fractions thereof) to characterize potential inverse agonists.

The invention claimed is:

1. An isolated cell line having American Type Culture Collection (A.T.C.C.) deposit designation PTA-5201.

2. A composition comprising cells of said cell line of claim 1.

3. A method of producing MCH receptor comprising the steps of culturing cells of said cell line of claim 1 for a time and under conditions sufficient for production of said MCH receptor.

4. A method of identifying an antagonist to the MCH receptor (MCHR) comprising the steps of:
   a) contacting cells of a cell line having A.T.C.C. deposit designation PTA-5201 with a test compound for a time and under conditions sufficient for said test compound to bind to MCHR produced by said cells of said cell line;
   b) adding MCH to said contacted cells of step a); and
   c) measuring intracellular calcium influx in said cells of step a) as compared to cells of said cell line which have not been exposed to said test compound and have been exposed to MCH, a decrease in said intracellular calcium influx in said cells of step a) as compared to said cells which have not been exposed to said test compound indicating said test compound is an antagonist to said MCH receptor.

5. A method of identifying an agonist to the MCH receptor comprising the steps of:
   a) contacting cells of a cell line having A.T.C.C. deposit designation PTA-5201 with a test compound for a time and under conditions sufficient for said test compound to bind to MCHR produced by said cells of said cell line;
   b) measuring intracellular calcium influx in said cells of step a) as compared to cells of said cell line which have not been exposed to said test compound, an increase in said intracellular calcium influx in said cells of step a) as compared to said cells which have not been exposed to said test compound indicating said test compound is an agonist to said MCH receptor.

6. A method of inhibiting activation of intracellular signaling by MCH comprising contacting cells of a cell line having A.T.C.C. deposit designation PTA-5201 with an antagonist to MCHR, wherein said antagonist is selected from the group consisting of T-226296 and SNAP-7941, for a time and under conditions sufficient for said antagonist to bind to MCHR produced by said cells of said cell line, said binding inhibiting activation of intracellular signaling by MCH subsequently added to said contacted cells.

7. A method of determining the binding affinity of MCH to MCHR comprising the steps of:
   a) contacting cells of a cell line baying A.T.C.C. deposit designation PTA-5201, or membranes thereof, with a conjugate, wherein said conjugate comprises MCH attached to a signal-generating compound capable of generating a detectable signal, for a time and under conditions sufficient for MCHR produced by said cells of said cell line to bind to said MCH of said conjugate;
   b) adding unlabelled MCH to said bound MCHR, for a time and under conditions sufficient for said unlabelled MCH to displace said conjugate; and
   c) detecting intensity of a signal generated by said signal-generating compound, wherein intensity of said signal is proportional to displacement of said conjugate by said unlabelled MCH and indicates binding affinity of said MCH to said MCHR.

8. A method of identifying a composition that inhibits binding of MCH to MCHR comprising the steps of:
   a) contacting cells of a cell line having A.T.C.C. deposit designation PTA-5201, or membranes thereof, with a test compound suspected of inhibiting binding of MCH to MCHR for a time and under conditions sufficient for said test compound to bind to MCHR produced by cells of said cell line;
   b) adding a conjugate to said contacted cells of step a), wherein said conjugate comprises MCH attached to a signal-generating compound capable of generating a measurable signal; and
   c) measuring inhibition of binding of MCH to MCHR by said test compound by quantifying said generated measurable signal and comparing said generated measurable signal to a control signal produced in the absence of said test compound, said control signal indicating zero percent inhibition of binding of MCH to MCHR, a smaller signal obtained with use of said test compound as compared to said control signal indicating said compound partially or completely inhibits binding of MCH to MCHR.

9. A method for producing a cell line that produces MCHR comprising the steps of:
   a) contacting IMR32 cells with DNA encoding $G\alpha_{16}$ and an antibiotic resistance marker;
   b) adding antibiotic for said antibiotic resistance marker to said contacted cells;
   c) isolating antibiotic resistant cells of step b) and propagating said cells;
   d) adding to said propagated cells said antibiotic at a higher concentration than used in step b); and
   e) isolating resulting cells of step d) and propagating said cells in order to produce a cell line that produces MCHR.

10. The method of claim 9 wherein said cell line has A.T.C.C. deposit designation PTA-5201.

11. A method of identifying an inverse agonist to the MCH receptor (MCHR) comprising the steps of:
   a) contacting cells of a cell line having A.T.C.C. deposit designation PTA-5201 with a test compound for a time and under conditions sufficient for said test compound to bind to MCHR produced by said cells of said cell line; and
   b) measuring intracellular calcium influx in said cells of step a) as compared to cells of said cell line which have not been exposed to Said test compound, a decrease in said intracellular calcium influx in said cells of step a) as compared to said cells which have not been exposed to said test compound indicating said test compound is an inverse agonist to said MCH receptor.

* * * * *

UNITED STATES PATENT AND TRADEMARK OFFICE
CERTIFICATE OF CORRECTION

PATENT NO. : 7,252,992 B2  
APPLICATION NO. : 10/463123  
DATED : August 7, 2007  
INVENTOR(S) : Dennis G. Fry et al.

Page 1 of 1

It is certified that error appears in the above-identified patent and that said Letters Patent is hereby corrected as shown below:

Col. 18, line 39  
 replace "baying"  
 with --having--.

Signed and Sealed this

Nineteenth Day of August, 2008

JON W. DUDAS  
*Director of the United States Patent and Trademark Office*